United States Patent [19]

Ellsworth et al.

[11] Patent Number: 5,504,104
[45] Date of Patent: Apr. 2, 1996

[54] TRICYCLIC PYRONE DERIVATIVES AS PROTEASE INHIBITORS AND ANTIVIRAL AGENTS

[75] Inventors: Edmund L. Ellsworth, Ann Arbor; Bradley D. Tait, Canton, both of Mich.

[73] Assignee: Warner-Lambert Company, Morris Plains, N.J.

[21] Appl. No.: 155,412

[22] Filed: Nov. 19, 1993

[51] Int. Cl.$^6$ .......................... A61K 31/35; C07D 311/78
[52] U.S. Cl. .......................... 514/455; 514/885; 549/280
[58] Field of Search .......................... 549/280; 514/885, 514/455

[56] References Cited

U.S. PATENT DOCUMENTS

| | | | |
|---|---|---|---|
| 2,034,303 | 3/1936 | Krzikalla et al. | 549/280 |
| 2,034,304 | 3/1936 | Krzikalla et al. | 549/280 |
| 2,596,107 | 5/1952 | Silverman et al. | 549/280 |
| 3,206,476 | 9/1965 | Collins | 549/292 |
| 3,818,046 | 6/1974 | Harris et al. | 549/292 |
| 3,931,235 | 6/1976 | Harris et al. | 549/292 |
| 4,963,581 | 10/1990 | Kanamara et al. | 514/455 |
| 5,100,914 | 3/1992 | Rendenbach-Mueller | 549/280 |
| 5,264,454 | 11/1993 | Meguro et al. | 514/455 |

FOREIGN PATENT DOCUMENTS

| | | |
|---|---|---|
| 3-227923 | 10/1991 | Japan . |
| 89/07939 | 9/1989 | WIPO . |
| WO9418188 | 8/1994 | WIPO . |

OTHER PUBLICATIONS

D. Richman, "Control of Virus Diseases," *45th Symposium of the Society for General Microbiology*, 1990, 261–313.
H. Toh, et al., *Nature*, 1985, 315:691.
J. Kay, et al., *Biochim. Biophys. Acta* 1: 1990, 1048.
C. Cameron, et al., *J. Biological Chem.* 168, 1993, 11711–11720.
M. Graves, *Structure and Function of the Aspartic Proteases*, 1991, 395–405.
C. Peng, et al., *J. Virol.*, 63: 1989, 2550–2556.
N. Kohl, et al., *Proc. Nat. Acad. Sci. USA*, 85:1988, 4689–4690.
J. C. Craig, et al, *Antiviral Research*, 16:1991, 295–305.
A. G. Tomasselli, et al., *Chimica Oggi*, 9:1991, 6–27.
T. Meek, *J. Enzyme Inhibition*, 6: 1992, 65–98.
R. Nagorny, et al, *AIDS*, 7:1993, 129–130.
D. P. Fairlie, et al., *Biochem. Biophys. Res. Comm.*, 188: 1992, 631–637.

*Primary Examiner*—C. Warren Ivy
*Assistant Examiner*—Amelia Owens
*Attorney, Agent, or Firm*—Elizabeth M. Anderson

[57] ABSTRACT

The present invention relates to novel substituted tricyclic pyrones and related structures which potently inhibit the HIV aspartyl protease blocking HIV infectivity. The tricyclic pyrone derivatives are useful in the development of therapies for the treatment of vital infections and diseases, including AIDS. The present invention is also directed to methods of synthesis of multifunctionalized tricyclic pyrones and of related structures.

10 Claims, No Drawings

TRICYCLIC PYRONE DERIVATIVES AS PROTEASE INHIBITORS AND ANTIVIRAL AGENTS

FIELD OF THE INVENTION

The present invention relates to tricyclic pyrone derivatives that are inhibitors of aspartyl proteases, in particular the aspartyl proteases found in retroviruses including Human Immunodeficiency Virus (HIV). The tricyclic pyrones are expected to have utility as antiviral agents, for the treatment of infection caused by HIV or other retroviruses employing aspartyl proteases, and to be useful in the treatment of diseases caused by the retroviruses, including AIDS.

BACKGROUND OF THE INVENTION

Acquired Immunodeficiency Syndrome (AIDS) was coined in 1982 to describe the clinical manifestations of immunodeficiency. The etiological agent of AIDS was later associated with a retrovirus, Human Immunodeficiency Virus (HIV), from the lentivirus subfamily. At least two infectious strains of HIV have been identified, HIV-1 and HIV-2. Here, HIV will be used as a general term describing all strains and mutants of the Human Immunodeficiency Virus. The detailed study of HIV has given rise to many approaches to antiviral drug development including inhibition of the viral aspartyl protease (D. Richman, *Control of Virus Diseases*, 45th Symposium of the Society for General Microbiology, 261–313 (1990)).

Aspartyl proteases have been found in many retroviruses including the Feline Immunodeficiency Virus (FIV), the Myeloblastosis Associated Virus (MAV), HIV, and the Rous Sarcoma Virus (RSV) [H. Toh et al., *Nature*, 315: 691 (1985); J. Kay, B. M. Dunn, *Biochim. Biophys. Acta*, 1: 1048 (1990); C. Cameron et al., *J. Biological Chem.*, 168: 11711–720 (1993)]. Since there are structural similarities among the known retroviral proteases, compounds which inhibit the HIV protease may well inhibit other retroviral proteases and thus be useful in the treatment of diseases caused by these viruses.

HIV aspartyl protease is responsible for post-translational processing of viral precursor polyproteins such as pol and gag. (M. Graves, *Structure and Function of the Aspartic Proteases*, 395–405 (1991)). Cleavage of these polyproteins by this protease is essential for maturation of the virus, since the proteolytic activity necessary for polyprotein processing cannot be provided by host cellular enzymes. An important finding has been that viruses which lack this protease, or contain a mutation which produces a defective protease, lack infectivity [C. Peng et al., *J. Virol*, 63: 2550–2556 (1989); and N. Kohl et al., *Proc. Natl. Acad. Sci. USA*, 85: 4686–4690 (1987)]. Thus, a selective HIV protease inhibitor has been shown to inhibit viral spread and the production of association cytopathic effects in cultures of acutely infected cells (J. C. Craig et al., *Antiviral Research*, 16: 295–305 (1991)). For this reason, inhibition of HIV protease is believed to be a viable approach to antiviral therapy.

HIV protease inhibitors have been extensively reviewed (see for example A. Tomasell et al., *Chimica Oggi*, 6–27 (1991) and T. Meek, *J. Enzyme Inhibition* 6: 65–98 (1992)). However, the majority of these inhibitors are peptides and thus unsuitable as drugs, due to the well known pharmacological deficiencies exhibited by most peptide drugs (biliary excretion, low-bioavailability and stability in physiological milieu, etc.). Nonpeptidic inhibitors of HIV protease are thus very important, since these may lead to useful therapeutic agents.

Hei 3-227923 claimed coumarins with anti-HIV activity. However, only 4-hydroxycoumarin was specifically described without discussion of mechanism of action.

World Patent 89/07939 claimed eight coumarin derivatives as HIV reverse transcriptase inhibitors with potential antiviral activity. These derivatives are hexachlorocoumarin, 7-acetoxycoumarin, and the structures shown below.

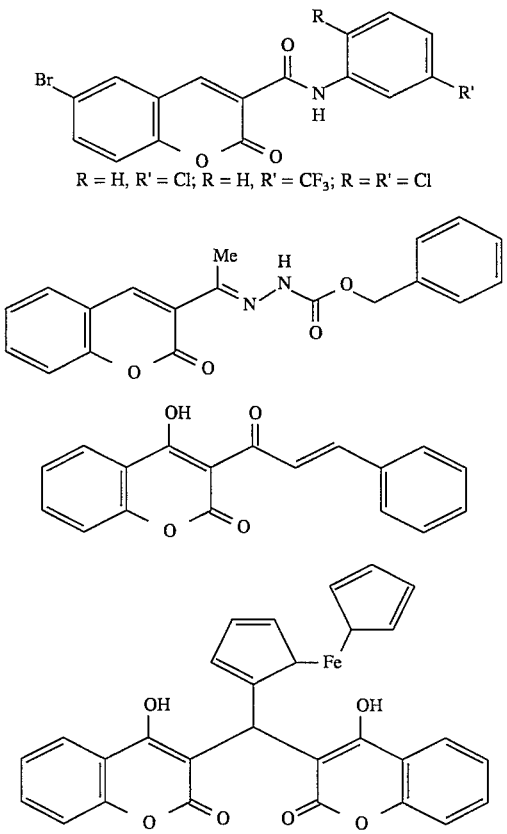

Warfarin (3-(α-acetonylbenzyl)-4-hydroxycoumarin), shown below, was reported by R. Nagorny et al. in *AIDS* 7: 129–130 (1993) as inhibiting cell-free and cell-mediated HIV infection. However, Warfarin was the only pyrone studied and its mechanism of action in HIV inhibition was not specified.

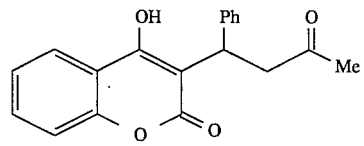

Selected flavones, structurally different from the pyrones of the present invention, were reported by Fairli et al., (*Biochem. Biophys. Res. Comm.*, 188: 631–637 (1992)) to be inhibitors of HIV-1 protease. These compounds are shown below.

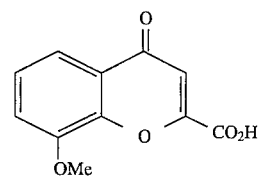
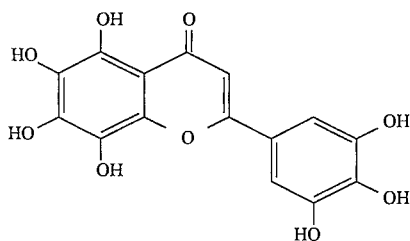

U.S. Pat. No. 3,206,476 describes several pyrones, specifically 3-substituted-4-hydroxy-6-aryl-2-pyrones, as antihypertensive agents. However, the range of substituents at the 3-position of these heterocycles is limited to halo and amino groups and alkanoylamino derivatives.

U.S. Pat. No. 3,818,046 describes several pyrone derivatives, specifically 4-hydroxypyrones with sulfur-containing carbon chains at the 3-position, as growth stunters and antimicrobial agents.

These pyrones, which are shown below, are substituted as follows: R=Me, M=H or alkali metal; R'=H, alkyl, phenyl, halophenyl, nitrophenyl, lower alkylphenyl, benzyl, phenethyl, naphthylmethyl, halobenzyl, lower alkylbenzyl, nitrobenzyl, propargyl, allyl, cyclohexyl lower alkyl, lower alkylthio, or adamantyl; and n is 0, 1, or 2.

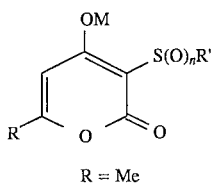

R = Me

A process for preparing the pyrones shown above is claimed in U.S. Pat. No. 3,931,235.

SUMMARY OF THE INVENTION

The present invention is based in great part on the extraordinary discovery of the inventors that novel tricyclic pyrones and related compounds, selected from a broad spectrum of tailored molecular structures, potently inhibit the HIV aspartyl protease blocking infection by HIV. The present invention is also based on the insights of the inventors regarding the mechanism of action of antiviral drugs, especially as revealed by their studies on structure-activity relationships characteristic of anti-HIV compounds that include tricyclic pyrones.

The invented pyrones are expected to be extremely useful in the development of treatments for infections caused by viruses, especially by retroviruses that rely on aspartyl protease activities for replication and infectivity. One such retrovirus is HIV. As virus blockers, the pyrones are also expected to be very useful in the treatment of diseases and syndromes associated with viral pathogens. One such syndrome is AIDS.

Efficient synthesis of the biologically active tricyclic pyrones, involving either de novo assemblies of the tricyclic pyrone nucleus or modifications of suitably functionalized tricyclic pyrones, are disclosed. Furthermore, many working examples outlining the preparation of specific tricyclic pyrones whose structures contain the desired functional groups in proper geometric arrangements are given.

The testing of specific tricyclic pyrones as inhibitors of the HIV aspartyl protease, based on a study of the hydrolysis of an undecapeptide enzyme substrate, and the testing of the tricyclic pyrones as inhibitors of viral growth and infectivity, based on the study of infection of H9 cell lines by the HIV-1$_{iiib}$ strain, are also disclosed. Striking enzyme inhibitions, at the nanomolar level, with corresponding anti-HIV activities, were observed.

The present inventors contemplate the preparation of pharmaceutically useful antiviral compositions comprising one or more of the invented tricyclic pyrones and related compounds and a pharmaceutically acceptably carrier. They also contemplate the use of these compositions, alone or in combination with other antiviral treatments, in the treatment of infections and diseases caused by retroviruses, including AIDS.

The present invention relates to compounds, or pharmaceutically acceptable salts thereof, of Formula 1.

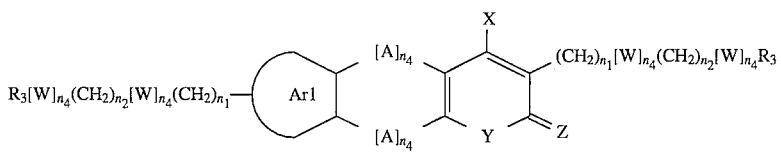

1 wherein

X is $OR_1$, $NHR_1$, SH, $CH_2OR_1$, or $CO_2H$ wherein $R_1$ is hydrogen or $COR_2$ wherein $R_2$ is a straight chain alkyl moiety 1 to 5 carbon atoms in length, a branched alkyl moiety containing three to five carbon atoms, a cyclic alkyl moiety containing three to six carbon atoms, phenyl, or a hydrogen atom;

Y is oxygen or sulfur;

Z is oxygen or sulfur;

W is oxygen, $NR_3$, $C(R_3)_2$, $NCO(V)_{n4}R_3$, CO, HC=CH, $S(O)_{n3}$, C≡C, $NR_3COV_{n4}$, or $CR_3OR_3$ wherein V is oxygen, sulfur, $NR_3$ or $CHR_3$ wherein $R_3$ is hydrogen, $(CH_2)_{n3}R_4$, or $(CH_2)_{n3}Ar$ wherein $R_4$ is hydrogen, a straight or branched alkyl moiety containing one to five carbon atoms, a cyclic alkyl moiety containing 3 to 6 carbon atoms, phenyl or the substituted derivatives thereof wherein the substituents are one or more of $CO_2R_2$, $CON(R_2)_2$, F, $OR_2$, phenyl, naphthyl, or $CF_3$;

Ar is a 5- or 6-membered ring containing from 0 to 3 heteroatoms, a fused ring of 8–10 atoms or the substituted derivatives thereof wherein the substituents are of F, Cl, Br, $OR_4$, $N(R_4)_2$, $CO_2R_4$, CON $(R_4)_2$, $COR_4$, $R_4$, $OCH_2O$, $OCH_2CH_2O$, or C≡N;

Ar1 is a 5- or 6- membered ring of 0 to 2 heteroatoms or a substituted derivative thereof wherein the substituents are of those listed for Ar above;

n1, n2, n3 and n4 are integers of from 0 to 4, 0 to 3, 0 to 2, and 0 to 1, respectively, with the provisos that n2 is zero when an intra-chain n4 is zero, and n2 is 2 to 4 when two intra-chain groups W are heteroatoms;

A is $T_{n4}NR_3T_{n4}$, $T_{n4}CONR_3T_{n4}$, $T_{n4}CO_2T_{n4}$, $T_{n4}OT_{n4}$, $T_{n4}COT_{n4}$, $T_{n4}SO_{n3}T_{n4}$, or $T_{n4}C(R_3)_2T_{n4}$ wherein $T=C(R_3)_2$ and the central ring of the tricycle is a 5-, 6-, 7-, or 8-membered ring.

Preferred compounds of the instant invention are those of Formula 1 above wherein X is hydroxy;
Z is oxygen;
Y is oxygen or sulfur;
W is oxygen, $NR_3$, $C(R_3)_2$, $S(O)_{n3}$, $CR_3OR_3$, or $CH=CH$ wherein $R_3$ is hydrogen, $(CH_2)_{n3}R_4$, or $(CH_2)_{n3}Ar$; $R_4$ is hydrogen, unsubstituted or substituted straight or branched alkyl containing 1 to 5 carbon atoms, cycloalkyl containing 3 to 6 carbon atoms, or phenyl wherein the substituents are of F, $CO_2H$, OMe, OH, $OCH_2CH_3$, or phenyl;
Ar1 is phenyl, pyridine, furan, thiophene or cyclohexane;
Ar is unsubstituted or substituted phenyl, or a 5- or 6-membered heterocycle with 1 or 2 heteroatoms, wherein the substituents are of F, Cl, Br, $OR_4$, $CO_2R_4$, $R_4$ or $OCH_2O$;
n1, n2, n3 and n4 are integers of from 0 to 4, 0 to 3, 0 to 2, and 0 to 1 respectively;
the central ring of the tricycle is a 5-, 6- or 7-membered ring; and
A is $OCH_2$, $CH_2O$, O, $SO_{n3}CH_2$, $CH_2SO_{n3}$, $SO_{n3}$, $(CH_2)_3$, $CH_2OCH_2$, $CH_2CHR_3$, $CHR_3CH_2$, $CHR_3$, $CH_2CHOH$, $CHOHCH_2$, CHOH, $CH_2NR_3$, $NR_3CH_2$, or $NR_3$.

More preferred compounds of the instant invention are those of Formula 1 wherein X is hydroxy;
Z is oxygen;
Y is oxygen;
W is oxygen, sulfur, $NR_3$, or $C(R_3)_2$ wherein $R_3$ is H, $(CH_2)_{n3}R_4$, or $(CH_2)_{n3}Ar$;
Ar1 is phenyl;
Ar is unsubstituted or substituted phenyl, 2-, 3-, or 4-pyridyl, 2- or 3-furyl, or 1- or 2-indanyl wherein the substituents are of F, Cl, $OR_4$, $CO_2R_4$, $R_4$, or $OCH_2O$ wherein $R_4$ is H, or unsubstituted or substituted $CH_3$, $CH_2CH_3$, $(CH_2)_3$, $(CH_3)_2CH$, $(CH_3)CHCH_2$, or $C_6H_5$ wherein the substituents are of $CO_2H$, F, OMe, OH, or $CF_3$;
n1, n2, n3 and n4 are integers of from 0 to 2, 0 to 3, 0 to 2, and 0 or 1 respectively;
the central ring of the tricycle is a 5- or a 6-membered ring; and
A is $CH_2$, $OCH_2$, $CH_2O$, $SO_{n3}CH_2$, $CH_2SO_{n3}$, O, $SO_{n3}$, $CH_2$, CHR, or $CHR_3CH_2$.

The most preferred compounds of the instant invention are the following:

5,6-Dihydro-4,8-dihydroxy-3-[(phenylmethyl)thio]-2H-naphtho[1,2-]pyran-2-one;

6,7-Dihydro-4-hydroxy-3-[(phenylmethyl)thio]-benzo[6,7]cyclohepta[1,2-b]pyran-2(5H)-one;

4-Hydroxy-3-[(phenylmethyl)thio]-2H,5H-pyrano[3,2-c][1]benzopyran-2-one;

Hydroxy-3-[(2-phenoxyethyl)thio]indeno[1,2-b]pyran-2(5H)-one;

5,6-Dihydro-4-hydroxy-9-(phenylmethoxy)-3-[(phenylmethyl)thio]-2H-naphtho[1,2-b]pyran-2-one;

5,6-Dihydro-4-hydroxy-7,9-dimethyl-3-[phenylmethyl)thio]-2H-naphtho[1,2-b]pyran-2-one;

4,8-Dihydroxy-3-[(phenylmethyl)thio]indeno[1,2-b]pyran-2(5H)-one;

5,6-Dihydro-4-hydroxy-3-[(phenylmethyl)thio]-2H-naphtho[1,2-b]pyran-2-one;

5,6-dihydro-4-hydroxy-6-methyl-3-[(phenylmethyl)thio]-2H-naptho[1,2-b]pyran-2 -one;

4-Hydroxy-3-[(2-phenylethyl)thio]indeno[1,2-b-]pyran-2(5H) -one;

4-Hydroxy-3-[(3-phenylpropyl)thio]-2H-naphtho[1,2-b]pyran-2-one;

4-Hydroxy-6-methyl-3-[(phenylmethyl)thio]-indeno[1,2-b]pyran-2(5H)-one;

[[5,6-Dihydro-4-hydroxy-2-oxo-3-[(phenylmethyl)-thio]-2-H-naphtho[1,2-b]pyran-8-yl ]oxy]acetic acid;

6-Bromo-4-hydroxy-3-[(phenylmethyl)thio]-indeno[1,2-b]pyran-2(5H)-one;

4-Hydroxy-3-[(2-phenylethyl)thio]-5-methylpyrano[3,2-b]indol-2-(5H)-one;

5,6-Dihydro-4,7-dihydroxy-3-[(phenylmethyl)thio]-2H-naphtho[1,2-b]pyran-2-one;

4-Hydroxy-3-[2-phenyl-1-[(phenylmethyl)thio]ethylindeno[1,2-b]pyran-2(5H)-one;

4-Hydroxy-3-[(3-methyl-1-phenylbutyl)thio]-indeno[1,2-b]pyran-2(5H)-one;

4-Hydroxy-3-(phenylmethoxy)indeno[1,2-b]pyran-2(5H)-one;

3-[Bis(phenylmethyl)amino]-4-hydroxyindeno[1,2-b]pyran-2(5H)-one;

4-Hydroxy-3-[[[(2-methylpropyl)phenylmethyl]-amino]methylindeno[1,2-b]pyran-2(5H)-one;

4,5-Dihydroxy-3-[3-methyl-1-[(phenylmethyl)thio]-butyl]indeno[1,2-b]pyran-2(5H)-one;

3-[1-[(3-Furanylmethyl)thio]-2-phenylethyl]-4,9-dihydroxyindeno[1,2-b]pyran-2(5H)-one;

Cis-[[(2,3-dihydro-1-hydroxy-1H-inden-2-yl)thio]methyl]-7,8 -difluoro-4-hydroxyindeno[1,2-b]pyran-2(5H)-one;

4-Hydroxy-5-(hydroxymethyl)-3-[(phenylmethyl)thio]indeno[1,2-b]pyran-2(5H)-one;

4-Hydroxy-3-[(phenylmethyl)thio]-purano[2',3';5,4]cyclopenta[1,2-b]pyridin-2(5H)-one;

4-Hydroxy-3-[(phenylmethyl)thio]-2H,5H-thieno[3',4':4,5]cyclopenta[1,2-b]pyran-2-one;

5,10-Dihydro-4,7,8-trihydroxy-3-[2-phenyl-1[(phenylmethyl)thio]ethyl]-2H-naphtho[2,3-b]pyran-2-one;

5,6-Dihydro-4,7,10-trihydroxy-3-[3-methyl-1-[(phenylmethyl)thio]butyl]-2H-naphtho[1,2-b]pyran-2-one;

5,6-Dihydro-4-hydroxy-3-[(3-methyl-1-phenylbutyl)thio]-2H-naphtho[1,2-b]pyran-2-one;

5,6-Dihydro-4,5-dihydroxy-6-(phenylmethoxyl-3-(phenylmethyl)thio]-2H-naphtho[1,2-b]pyran-2-one;

5,10-Dihydro-4-hydroxy-8-phenoxy-3-[(phenylmethyl)thio]-2H-naphtho[2,3-b]pyran-2-one;

3-[(2-Furanylmethyl)thio]-5,10-dihydro-4-hydroxy-2H-naphtho[2,3-b]pyran-2-one;

3-[[(5,6-Dihydro-4-hydroxy-2-oxo-2H-pyrano[2,3-f]quinolin-3-yl)thio]methyl]benzoic acid ethyl ester;

4,5-Dihydro-6-hydroxy-7-(2-phenoxyethyl)-8H-thieno[3'4':5,6]benzo[1,2-b]pyran-8-one;

5,6,6a,7,8,9,10,10a-Octahydro-4-hydroxy-3-[(2-phenylethyl)thio]-7-(phenylmethoxy)-2H-naphtho[12-b]pyran-2-one;

5,6-Dihydro-4-hydroxy-5-(hydroxymethyl)-3-[2-phenyl-1-[(phenylmelthyl)thio]ethyl-2H-naphtho [1,2-b]pyran-2-one;

4-Hydroxy-3-[(phenylmelthyl)thio]-,5,5-dioxide-2H6H-pyrano[3,2-c][2,1]benzothiazin-2-one;

4-Hydroxy-3-[(3-methyl-1-phenylbutyl)thio]-8-(phenylmethoxy)-2H-[1]benzothieno[3,2-b]pyran-2-one;

4-Hydroxy-3-[(phenylmethyl)thio]-6-methylindeno[1,2-b]pyran-2(5H)-one;

5,6-Dihydro-4,9-dihydroxy-3-[(phenylmethyl)thio]-2H-naphtho[1,2-b]pyran-2-one;

4-Hydroxy-3-[(phenylmethyl)thio]-2H,5H-[1]benzothiopyrano[4,3-b]pyran-2-one;

4-Hydroxy-3-[(phenylmethyl)thio]-2H,6H-[2]benzothiopyrano[4,3-b]pyran-2-one;

9-Chloro-5,6-dihydro-4,7-dihydroxy-3-[(phenylmethyl)thio]-2H-naphtho[1,2-b]pyran-2-one;

7-Fluoro-4-hydroxy-3-[(phenylmethyl)thio]indeno-[1,2-b]pyran-2(5H)-one;

[[2,5-Dihydro-4-hydroxy-2-oxo-3-[(phenylmethyl)-thio]indeno[1,2-b]pyran-8-yl]oxy]-acetic acid;

4-Hydroxy-3-[(phenylmethyl)thio]-6,8-dimethylindeno[1,2-b]pyran-2(5H)-one;

[[2,5-Dihydro-4-hydroxy-2-oxo-3-[(phenylmethyl)-thio]indeno[1,2-b]pyran-6-yl]oxy]-acetic acid;

3-[(Cyclopropylmethyl)thio]-4-hydroxyindeno[1,2-b]pyran-2(5H)-one;

4-Hydroxy-3-[(3-phenylpropyl)thio]indeno[1,2-b]pyran-2(5H)-one;

4-Hydroxy-3-[(2-phenylethyl)thio]-2H-naphtho[1,2-b]pyran-2-one;

4-Hydroxy-3-[phenylthio]indeno[1,2-b]pyran-2(5H)one; and

4-Hydroxy-3-[phenylthio]-2H-naphtho[1,2-b]pyran-2-one.

DETAILED DESCRIPTION OF THE INVENTION

Here, the term "alkyl", usually represented by an "R", means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl groups may contain one or more sites of unsaturation such as double or triple carbon-carbon bonds. The alkyl group is unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NH—, —$CO_2$R, —COR, aryl, or heteroaryl wherein alkyl (R), aryl, and heteroaryl are defined as herein.

The term "cycloalkyl", also represented by an "R", means a saturated hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain a single double bond. The cycloalkyl ring may be unsubstituted or substituted by from 1 to 3 substituents selected alkyl, alkoxy, thioalkoxy all as defined herein, hydroxy, thiol, nitro, halogen, amino, formyl, carboxyl, nitrile, —NH—CO—R, —CO—NHR—, —$CO_2$R, —COR, aryl, or heteroaryl wherein alkyl (R), aryl, and heteroaryl are defined as herein.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, or a fluarenyl group and the like, unsubstituted or substituted by 1 to 3 substituents selected from alkyl as defined above, alkoxy as defined above, thioalkoxy as defined above, hydroxy, thiol, nitro, halogen, amino, formyl, carboxy, nitrile, —NHCOR, —CONHR, —$CO_2$R, —COR, aryl, or heteroaryi wherein alkyl (R), aryl, and heteroaryl are defined as above.

The terms "heteroaryl" and "heterocycle", usually represented by an "Ar", mean a heteroaromatic radical, including a radical which consists of fused rings, which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3 -, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, thiophenyl, pyrolidinyl, piperidinyl, piperazinyl, morpholinyl, thiomorpholinyl, tetrahydrofuranyl; indanyl benzofuranyl, benzothiophenyl, benzisoxazolyl, coumarinyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino, carboxyl, nitrile, —NHCOR, —$CO_2$R, —COR, wherein alkyl in as defined above or phenyl.

"Halogen" is fluorine, chlorine, bromine or iodine.

Some of the compounds of Formula 1 are capable of further forming pharmaceutically acceptable acid-addition and/or base salts. All of these forms are within the scope of the present invention.

Pharmaceutically acceptable acid addition salts of the compounds of Formula 1 include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al., "Pharmaceutical Salts," *Journal of Pharmaceutical Science,* 66: 1–19 (1977).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts," *Journal of Pharmaceutical Science,* 66; 1–19 (1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a compound of Formula 1.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of a retroviral protease, as agents for the treatment of infections caused by a retrovirus including HIV, or as agents for the treatment of diseases due to AIDS, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

General Synthetic Approaches to Tricyclic Pyrone Derivatives

Scheme I, shown below, illustrates the preparation of tricyclic pyran-2-one derivatives.

SCHEME I

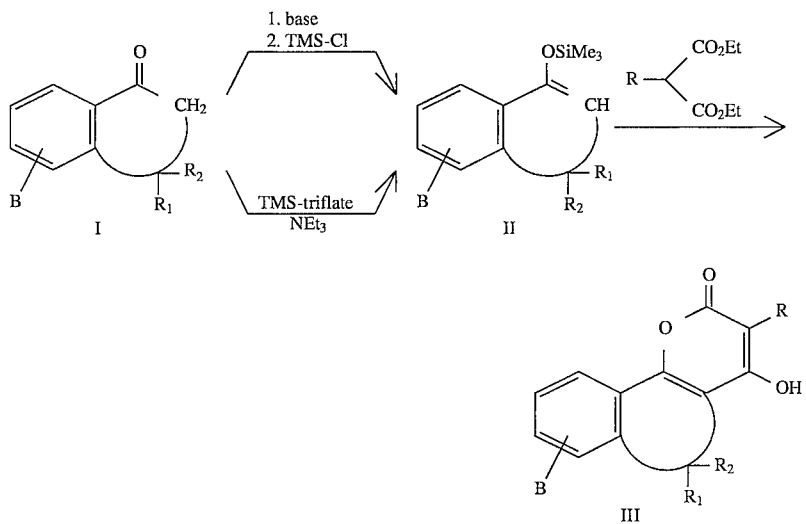

Ketone I, is treated with a suitable base, preferably a lithium amide base such as lithium diisopropylamide or lithium bis(trimethylsilyl)amide, at −78° C. to −45° C., in ether or THF solution, and quenched with chlorotrimethylsilane at −78° C. to 0° C. producing the silyl enol ether II. Alternatively, ketone I is reacted with trimethylsilyl trifluoromethanesulfonate at −30° C. to +10° C. in dichloromethane in the presence of a suitable base such as triethylamine. Silyl enol ether II is isolated, combined with the desired malonate, and the mixture is heated at 130°–160° C. for 10–24 hours, producing tricyclic pyrone III.

For purposes of the above and other syntheses of the compounds of the present invention, reactive functional groups present in starting materials, reaction intermediaters, or reaction products may be protected during chemical reactions using protecting groups which render the reactive functional groups substantially inert to the reaction conditions. (See for example, *Protective Groups in Organic Synthesis,* 2 ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after completion of the synthetic reaction of interest, by procedures known to those skilled in the art. For example, the BOC group may be removed by acidolysis, the trityl group by hydrogenolysis, TBDMS by treatment with fluoride ions, and TCEC by treatment with zinc.

A second approach to the desired pyrones is outlined in Scheme II.

SCHEME II

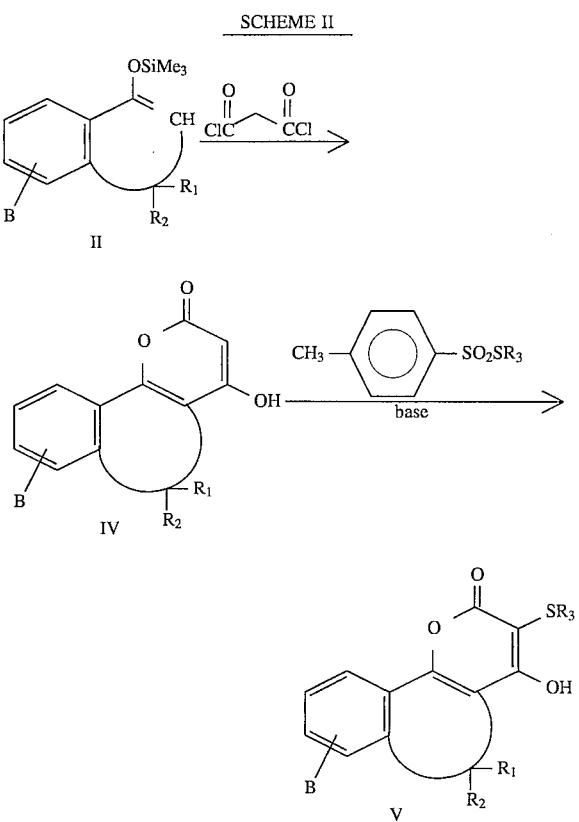

Silyl enol ether II is reacted with malonyl dichloride at −78° C. to −50° C., preferably −78° C., in a dry solvent such as ether, to give cyclized pyrone IV. Elaboration of IV to 3-thio derivatives V may be effected by reaction with an appropriately substituted p-toluenethiosulfonate, in a suitable solvent, such as ether, DMF (dimethylformanide), or ethanol, containing a suitable base such as sodium hydroxide.

Scheme III describes the preparation of additional classes of tricyclic pyran-2-ones.

SCHEME III

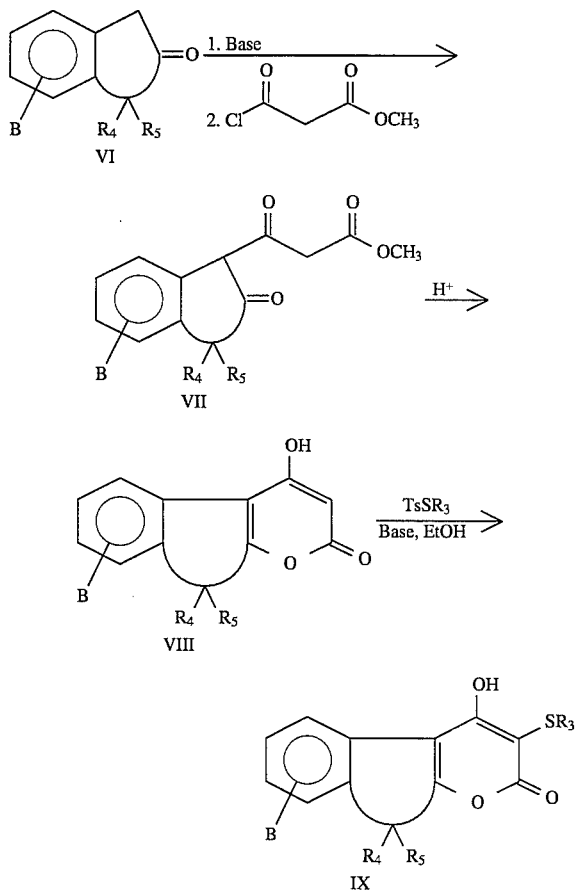

Ketone VI is treated with an appropriate base, e.g. triethylamine in an inert solvent at −78° C. to 0° C., to give the enolate which is acylated with methyl malonyl chloride at 0° C. to 20° C furnishing dione ester VII. Cyclization VII in the presence of strong acid, e.g. sulfuric acid, at 25°–50° C. furnishes tricyclic pyrone VIII, which may be further elaborated to the 3-thio derivatives, such as IX, as shown above in Scheme II.

SYNTHESIS OF SPECIFIC TRICYCLIC PYRONE DERIVATIVES

EXAMPLE A

4-Hydroxyindeno[1,2-b]pyran-2(5H)-one

A solution of 1-indanone (3.00 g, 22.7 mmol) in THF (25 mL) was cooled to −78° C. ($N_2$ atmosphere) and treated with a THF solution of lithium diisopropylamine (34.1 mL, 25.0 mmol). The solution was warmed to 0° C., allowed to stir for 10 minutes then treated with trimethylsilylchloride (2.90 mL, 22.7 mmol). The mixture was allowed to warm to ambient temperature and stir for 10 minutes before being quenched into a mixture of diethyl ether (50 mL) and saturated aqueous $NaHCO_3$ (20 mL). The layers were separated and the organic layer washed with a 1:1 mixture of brine: saturated $NaHCO_3$ (20 mL). The ethereal solution was then dried with $Na_2SO_4$ and the solvent removed in vacuo. The residue was then dissolved in diethyl ether (10.0 mL) and cooled to −78° C. ($N_2$ atmosphere) where a solution of malonyldichloride (0.74 mL, 7.6 mmol) in diethyl ether (10.0 mL), precooled to −78° C., was added via cannula. The mixture was allowed to slowly warm to ambient temperature where it was stirred for 15 hours. The resulting slurry was then quenched with 2.0N HCl (20.0 mL) and extracted with ethyl acetate (3×100 mL) being sure to collect all solids. The layers were then combined and diluted with acetone to provide a homogenous solution which was dried with $Na_2SO_4$. The solvent was then removed in vacuo and the resulting solid recrystallized from acetone-hexanes to provide the title compound (0.846 g, m.p. 241°–245° C. (dec.)). 'H NMR (400 MHz, DMSO-$d_6$) δ 12.068 (bs, 1H), 8,329-7,628 (m, 2H), 7.482-7.450 (m, 2H), 5.398 (s, 1H), 3.664 (s, 2H).

EXAMPLE B

4-Hydroxy-2H-naphtho[1,2-b]pyran-2-one

A solution of 1-tetralone (5.00 g, 34.2 mmol) in $CH_2Cl_2$ (20.0 mL) was cooled to 0° C. ($N_2$ atmosphere) and treated with triethylamine (4.40 g, 39.3 mmol) followed by trimethylsilyltriflate (8.00 mL, 37.6 mmol). The solution was then warmed to ambient temperature, allowed to stir for 15 min., and subsequently quenched into a mixture of diethyl ether (50 mL) and saturated aqueous $NaHCO_3$ (20 mL). The layers were separated and the organic layer washed with a 1:1 mixture of brine: saturated $NaHCO_3$ (20 mL). The ethereal solution was then dried with $Na_2SO_4$ and the solvent removed in vacuo. The resulting silyl enol ether was then transferred to a flask containing $CH_2Cl_2$ (20.0 mL) and the mixture cooled to 0° C. ($N_2$ atmostphere). Methylmalonylchloride (2.45 mL, 20.5 mmol) was then added via syringe and the resulting mixture stirred for 1 h at 0° C. followed by 2 h at ambient temperature. The mixture was then poured into a 1:1 mixture of ethyl acetate: saturated ammonium chloride. The organic layer was separated and concentrated in vacuo. The resulting oil was then treated with concentrated $H_2SO_4$ and the mixture stirred for 15 h at room temperature. The mixture was then diluted with $H_2O$ and filtered to provide a solid which was passed through a pad of $SiO_2$ with $CH_2Cl_2$ and the solvent removed in vacuo to provide a solid (1.87 g, m.p. 185°–186° C. (dec.)). 'H NMR (250 MHz, DMSO-$d_6$) δ 12.100 (bs, 1H), 7.653-7.618 (m, 1H), 7.415-7.323 (m, 3H), 5.438 (s, 1H), 2.881 (t, 2H, J=7.5 Hz), 2.615 (t, 2H, J=7.5 Hz).

EXAMPLE C

Methyl [(2,3-dihydro-3-oxo-1H-inden-6-yl)oxy]acetate

A mixture of 6-hydroxyindanone (0.850 g, 5.74 mmol), $CsCO_3$ (2.43 g, 7.46 mmol), and acetone (25.0 mL) under an $N_2$ atmosphere was treated with methylbromoacetate (0.690 mL, 7.46 mmol) and the mixture heated to reflux for 5 h. The mixture was then allowed to cool to ambient temperature, diluted with $H_2O$ and extracted with $CH_2Cl_2$ (3×50 mL). The organic layers were combined, dried with $Na_2SO_4$, and the solvent removed in vacuo to provide the title compound (1.25 g, m.p. 91°–93° C.). 'H NMR (400 MHz, DMSO-$d_6$) δ 7.501 (d, 1H, J=8.5 Hz), 7.309 (dd, 1H, J=2.5 Hz, 8.5 Hz), 7.059 (d, 1H, J=2.5 Hz), 4.888 (s, 2H), 3.698 (s, 3H), 3.020 (dd, 2H, J=5 Hz, J=5 HZ), 2.660-2.631 (m, 2H).

EXAMPLE D

Methyl [(2,3-dihydro-1-oxo-1H-inden-4-yl)oxy]acetate

The title compound (1.84 g, m.p. 106°–108° C.) was prepared in a similar manner to that demonstrated in the preparation methyl [(2,3-dihydro-3-oxo-1H-inden-6-yl)oxy]acetate (Example C) using the following: 4-hydroxyindan-1-one (4.37 g, 20.7 mmol), CsCO$_3$ (13.47 g, 41.34 mmol), methylbromoacetate (3.80 mL, 41.3 mmol), acetone (100.0 mL). $^1$H NMR (400 MHz, DMSO-d$_6$) δ 7.367 (t, 1H, J=7.7 Hz), 7.246 (d, 1H, J=7.7 Hz), 7.168 (d, 1H, J=7.7 Hz), 4.961 (s, 2H), 3.712 (s, 3H), 3.008 (dd, 2H, J=5.5 Hz, J=5.5 Hz), 2.659-2.630 (m, 2H).

EXAMPLE E

2,3-Dihydro-6-(phenylmethoxy)-1H-inden-1-one

A solution of 6-hydroxyindan-1-one (1.60 g, 10.8 mmol (M. Phialas, P. G. Sammes, P. D. Kennewell, R. Westwood, *J. Chem. Soc. Perkin Trans.* 1: 687 (1984)), benzyl alcohol (1.23 mL, 11.9 mmol), triphenylphosphine (4.25 g, 16.2 mmol) under a N$_2$ atmosphere in THF (100.0 mL) was treated with diethyl azodicarboxylate (2.55 mL, 16.2 mmol). The mixture was allowed to stir for 4 h then quenched with H$_2$O. The mixture was then extracted with hexane (3×50 mL), the organic layers combined, dried with Na$_2$SO$_4$, and the solvent removed in vacuo. The residue was then submitted to column chromatography (SiO$_2$ 260–400 mesh, 4:1 hexanes: ethyl acetate) to provide the title compound (1.852 g, m.p. 99°–101° C.) as a solid. $^1$H NMR (400 MHz, CDCl$_3$) δ 7.445-7.305 (m, 6H), 7.272-7.247 (m, 2H), 5.084 (s, 2H), 3.079 (m, 2H), 2.723-2.694 (m, 2H).

EXAMPLE F

3,4-Dihydro-6-(phenylmethoxy)-1(2H)-naphthalenone

The title compound (1.30 g, m.p. 95°–97° C.) was prepared in a similar manner to that demonstrated in the preparation of 2,3-dihydro-6-(phenylmethoxy)-1H-inden-1-one (Example E) using the following: 6-hydroxytetralone (1.20 g, 7.40 mmol, benzyl alcohol (0.77 mL, 7.40 mmol), triphenylphosphine (2.90 g, 11.0 mmol), diethylazodicarboxylate (1.70 mL, 11.0 mmol), THF (20.0 mL). $^1$H NMR (400 MHz, CDCl$_3$) δ 8.012 (d, 1 H<J=9 Hz), 7.439-7.320 (m, 5H), 6.890 (dd, 1H, J=2.5 Hz, J=9 Hz), 6.787 (d, 1H, J=2.5 Hz), 5.113 (s, 2H), 2.917 (t, 2H, J=6 Hz), 2.607 (t, J =6 Hz ), 2.111 (quint., 2H, J=6 Hz ).

EXAMPLE G

(Cyclopropylmethyl)-p-toluenethiosulfonate

To a solution of methylcyclopropyl bromide (4.00 g, 29.6 mmol) in ethanol (20.0 mL) was added potassium thiotosylate (10.0 g, 44.4 mmol) and the mixture heated to 90° C. for 10 h. The mixture was then quenched into a 1:1 mixture of H$_2$O (50.0 mL) and diethyl ether (50.0 mL). The layers were separated and the organic layer washed with brine (50.0 mL). The organic layer was then dried with MgSO$_4$ and concentrated in vacuo to yield the title compound as a solid (5.2 g, m.p. 46°–48° C.). $^1$H NMR (400 MHz, CDCl$_3$) δ 7.816 (d, 2H, J=8.8 Hz), 7.308 (d, 2H, J =8.8 Hz), 2.945 (d, 2H, J=7.6 Hz), 2.451 (s, 3H), 1.010-0.933 (m, 1H), 0.592-0.545 (m, 2H), 0.236-0.197 (m, 2H).

EXAMPLE 1

4-Hydroxy-3-[(phenylmethyl)thio]-indeno[1,2-b]pyran-2(5H)-one

A solution of 1-indanone (1.0 g. 7.57 mmol) in THF (25 mL) was cooled to −78° C. (N$_2$ atmosphere) and treated with a 1.0M solution of lithium hexamethyldisilazane (8.3 mL, 8.3 mmol) in THF. The solution was warmed to 0° C., allowed to stir for 15 minutes then treated with trimethylsilylchloride (0.98 mL, 7.70 mmol). The reaction mixture was then allowed to stir for 15 h (ambient temperature) and subsequently quenched into a mixture of diethyl ether (50 mL) and saturated aqueous NaHCO$_3$ (20 mL). The layers were separated and the organic layer washed with a 1:1 mixture of brine: saturated NaHCO$_3$ (20 mL). The ethereal solution was then dried with Na$_2$SO$_4$ and the solvent removed in vacuo. The resulting silyl enol ether was then transferred to a flask containing diethyl 2-(thiobenzyl)propane-1,3-dioate (1.40 g, 5.00 mmol), the resulting mixture heated to 160° C. for 16 h. and then allowed to cool to room temperature where it was diluted with diethyl ether (20 mL) and extracted with saturated Na$_2$CO$_3$ (3×20 mL). The aqueous layer was then acidified with conc. HCl to pH 0 and then extracted with ethyl acetate (3×100 mL). The organic layers were combined, dried with Na$_2$SO$_4$ and the solvent removed in vacuo. The resulting residue was then submitted to chromatography (SiO$_2$-230 to 400 mesh, 100% CH$_2$Cl$_2$ to 1% MeOH/CH$_2$Cl$_2$) to provide a solid which was recrystallized from acetone/hexanes to provide 0.313 g (m.p. 187°–188° C.) of the title compound. $^1$H NMR (400 MHz, DMSO-d$_6$) δ 7.674-7.633 (m, 2H), 7.484-7.462 (m, 2H), 7.291-7.173 (m, 5 H), 3.990 (s, 2H), 3.677 (s, 2H).

EXAMPLE 2

4-Hydroxy-7-methoxy-3-[(phenylmethyl)thio]indeno[1,2-b]pyran-2(5H)-one

The title compound (0.298 g, m.p. 186°–187° C.) was prepared in a similar manner to that demonstrated in the preparation of 4-hydroxy-3-[(phenylmethyl)thiol)indeno[1,2-b]pyran-2(5H)-one (Example 1) using the following: 5-methoxy-1-indanone (4.00 g, 24.7 mmol), lithium diisopropylamine (50.7 mL, 27.1 mmol), trimethylsilylchloride (3.30 mL, 25.9 mmol), THF (20.0 mL), diethyl 2-(thiobenzyl)propane-1,3-dioate (2.15 g, 8.22 mmol). $^1$H NMR (400 MHz, CDCl$_3$) δ 7.661 (d, 1H, J=8 Hz), 7.253-7.192 (m, 5H), 7.074 (s, 1H), 6.998 (dd, 1H, J=3 Hz, 8 Hz), 3.932 (s, 2H), 3.878 (s, 3H), 3.536 (s, 2H).

EXAMPLE 3

4,8-Dihydroxy-3-[(phenylmethyl)thio]-indeno[1,2-b]pyran-2(5H)-one

The title compound (0.58 g, m.p. 237°–239° C.) was prepared isolated in a similar manner to that demonstrated in the preparation of 4-hydroxy-3-[(phenylmethyl)thiol]indeno[1,2-b]pyran-2(5H)-one (Example 1) using the following: 6-hydroxy-1-indanone (2.00 g, 13.5 mmol, M. Phialas et al., *J. Chem. Soc. Perkin Trans.* 1, 687, 1984), lithium diisopropylamine (52.7 mL, 29.7 mmol), trimethylsilylchloride (3.60 mL, 3.6 mmol), THF (15.0 mL), diethyl 2-(thiobenzyl)propane-1,3-dioate (1.77 g, 6.76 mmol). $^1$H NMR (400 MHz, DMSO-d$_6$) δ 9.770 (bs, 1H), 7.416 (d, 1H, J=8 Hz), 7.278 7.158 (m, 5H), 6.977 (d, 1H, J=2 Hz), 6.877 (dd, 1H, J=Hz, 8 Hz), 3.975 (s, 2H), 3.541 (s, 2H).

EXAMPLE 4

5,6-Dihydro-4-hydroxy-3-[(phenylmethyl)thio]-2H-naphtho[1,2-b]pyran-2-one

A solution of 1-tetralone (3.00 mL, 22.6 mmol) in $CH_2Cl_2$ (50.0 mL) was cooled to 0° C. ($N_2$ atmosphere) and treated with triethylamine (4.10 mL, 29.3 mmol) followed by trimethylsilyltriflate (5.23 mL, 27.0 mmol). The solution was then warmed to ambient temperature, allowed to stir for 15 min., and subsequently quenched into a mixture of diethyl ether (50 mL) and saturated aqueous $NaHCO_3$ (20 mL). The layers were separated and the organic layer washed with a 1:1 mixture of brine:saturated $NaHCO_3$ (20 mL). The ethereal solution was then dried with $Na_2SO_4$ and the solvent removed in vacuo. The resulting silyl enol ether was then transferred to a flask containing diethyl 2-(thiobenzyl)propane-1,3-dioate (1.97 g, 7.52 mmol), the mixture heated to 160 ° C. for 16 h. then allowed to cool to room temperature where it was submitted to chromatography ($SiO_2$-230 to 400 mesh, 100% $CH_2Cl_2$ to 1% $MeOH/CH_2Cl_2$) to provide the title compound as a solid (0.619 g, m.p. 57°–60° C.) which was dried in vacuo. $^1H$ NMR (400 MHz, $CDCl_3$) δ 7.917-7.900 (dd, 1 H, J=2 Hz), 7.363-7.329 (m, 2H), 7.273-7.191 (m, 6H), 3.961 (s, 2H), 2.883 (t, 2H, J=8 Hz), 2.614 (t, 2H, 8 HZ).

EXAMPLE 5

5,6-Dihydro-4-hydroxy-6-methyl-3-[(phenylmethyl)thio]-2H-naphthol[1,2-b]pyran-2-one A solution of 4-methyl-l-tetralone (3.00 g, 18.8 mmol) in $CH_2Cl_2$ (50.0 mL) was cooled to 0° C. ($N_2$ atmosphere) and treated with triethylamine (3.9 mL, 28 mmol) followed by trimethylsilyltriflate (3.99 mL, 20.6 mmol). The solution was then warmed to ambient temperature, allowed to stir for 15 min., and subsequently quenched into a mixture of diethyl ether (50 mL) and saturated aqueous $NaHCO_3$ (20 mL). The layers were separated and the organic layer washed with a 1:1 mixture of brine:saturated $NaHCO_3$ (20 mL). The ethereal solution was then dried with $Na_2SO_4$ and the solvent removed in vacuo. The resulting silyl enol ether was then transferred to a flask containing diethyl 2-(thiobenzyl) propane-1,3-dioate (1.97 g, 7.52 mmol). The mixture was then heated to 160° C. for 16 h. and allowed to cool to room temperature where it was diluted with diethyl ether (20 mL) and extracted with saturated $Na_2CO_3$ (3×20 mL). The combined aqueous extracts were acidified with conc. HCl to pH 0 and extracted with dichloromethane (3×100 mL). The organic layers were combined, dried with $Na_2SO_4$ and the solvent removed in vacuo. The resulting residue was then submitted to chromatography ($SiO_2$-230 to 400 mesh, 100% $CH_2Cl_2$ to 0.5% $MeOH/CH_2Cl_2$) to provide the title compound (0.604 g, m.p. 57°–60° C.). $^1H$ NMR (400 MHz, $CDCl_3$) δ 7.918 (dd, 1H, J=1 Hz, 8 Hz), 7.440 (m, 2H), 7.331 (td, 1H, J=1 H, 8 Hz), 7.260-7.179 (m, 6H), 3.954 (d, 2H, J=2 Hz), 3.035 (sex, 1H, J =7 Hz), 2.706 (dd, 1H, J=7 Hz), 2.434 (dd, 1H, J =7 Hz, 16 Hz), 1.222 (d, 1H, J=7 Hz).

EXAMPLE 6

5,6-Dihydro-4-hydroxy-7,9-dimethyl-3-[(phenylmethyl)thio]-2H-naphtho[1,2-b]pyran-2-one The title compound (0.639 g, m.p. 138°–140° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 5,7-dimethyl-1-tetralone (2.50 g, 14.4 mmol), triethylamine (3.00 mL, 21.5 mmol), trimethylsilyltriflate (2.90 mL, 15.1 mmol), dichloromethane (20.0 mL), diethyl 2-(thiobenzyl)propane-1,3-dioate (1.25 g 4.78 mmol). $^1H$ NMR (400 MHz, $CDCl_3$) δ 7.631 (s, 1H), 7.391 (s, 1H), 7.259-7.179 (m, 5H), 7.061 (s, 1H), 3.950 (s, 2H), 2.767 (t, 2H, J=8 Hz), 2.577 (t, 2H, J=8 Hz), 2.335 (s, 3H), 2.269 (s, 3H).

EXAMPLE 7

9-Ethyl-5,6-dihydro-4-hydroxy-3-[(phenylmethyl)thio]-2H-naphtho[1,2-b]pyran-2-one The title compound (0.622 g, m.p. 163°–165° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 7-ethyl-1-tetralone (2.00 g, 11.4 mmol, Burnham et al., *J. Org. Chem.* 39: 1416 (1974)), triethylamine (2.40 mL, 17.2 mmol), trimethylsilyltriflate (2.40 mL, 12.6 mmol), dichloromethane (20 mL) diethyl 2-(thiobenzyl) propane-1,3-dioate (1.00 g, 3.83 mmol). $^1H$ NMR (400 MHz, DMSO-$d_6$) δ 7.493 (s, 1H) , 7.275-7.197 (m, 8H), 3.967 (s, 2H), 2.809 (t, 2H, J=2 Hz), 2.645 (q, 2H, J=8 Hz), 2.586-2.520 (m, 2H), 1.194 (t, 3H, 8 Hz).

EXAMPLE 8

5,6-Dihyro-4-hydroxy-9-(phenylmethoxy)-3-[(phenylmethyl)thio]-2H-naphtho[1,2-b]pyran-2-one The title compound (0.174 g, m.p. 65°–67° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 7-benzyloxy-1-tetralone (1.20 g, 5.11 mmol), triethylamine (1.0 mL, 7.7 mmol), trimethylsilyltriflate (1.0 mL, 5.6 mmol), dichloromethane (15 mL) diethyl 2-(thiobenzyl)propane-1,3-dioate (0.670 g, 2.56 mmol). $^1H$ NMR (400 MHz, DMSO-$d_6$) δ 11.25 (bs, 1H), 7.482-7.191 (m, 12H), 7.051 (dd, 1H, J=3 Hz, 8 Hz), 5.166 (s, 2H), 3.979 (s, 2H, 2.777 (t, 2H, J=7 Hz), 2.571 (t, 2H, J=7 Hz).

EXAMPLE 9

5,6-Dihydro-4,8-dihydroxy-3-[(phenylmethyl)thio]-2H-naphtho[1,2-b ]pyran-2-one The title compound (0.492 g, m.p. 223°–224° C.) was prepared in a similar manner to that demonstrated in the preparation of 5,6-dihydro-4-hydroxy-6-methyl-3-[(phenylmethyl)thio ]-2H-naphtho[1,2-b]pyran-2-one (Example 5) using the following: 7-hydroxy-1-tetralone (1.75 g, 10.8 mmol, Y. Oikawa, *J. Org. Chem.* 42:1213 (1977)), triethylamine (4.50 mL, 32.4 mmol), trimethylsilyltriflate (4.60 mL, 22.0 mmol), dichloromethane (20 mL) diethyl 2-(thiobenzyl)propane-1,3-dioate (1.41 g, 5.40 mmol) . $^1H$ NMR (400 MHz, DMSO-$d_6$) δ 10.995 (bs, 1H), 10.097 (s, 1H), 7.506 (d, 1H, J=8 Hz), 7.293-7.194 (m, 5H), 6.743 (dd, 1H, J=2 Hz, 8 Hz), 6.698 (d, 1H, J=2 Hz), 3.943 (s, 2H), 2.768 (t, 2H, J=7 Hz), 2.546 (t, 2H, J=7 Hz).

EXAMPLE 10

4,6-Dihydroxy-3-[(phenylmethyl)thio]-indeno[1,2-b]pyran-2(5H)-one

The title compound (0.328 g, m.p. 230°–232° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 4-hydroxy-1-indanone (1.58 g, 10.7 mmol, J. P. Gesson, *Tetrahedron Lett.*, 24:3095 (1983)), triethylamine (4.40 mL, 32.0 mmol), trimethylsilyltriflate (4.50 mL, 23.5 mmol), dichloromethane (40 mL) diethyl 2-(thiobenzyl)propane-1,3-dioate (1.41 g, 5.33 mmol). $^1$H NMR (400 MHz, DMSO-$d_6$) δ 11.752 (bs, 1H), 9.949 (s, 1H), 7.320-7.158 (m, 6H), 7.135 (d, 1H, J=8 Hz), 6.917 (d, 1H, J=8 Hz), 3.978 (s, 2H), 3.518 (s, 2H).

EXAMPLE 11

4-Hydroxy-8-(phenylmethoxy)-3-[(phenylmethyl)thio]indeno[1,2-b]pyran-2(5H)-one The title compound (0.313 g, m.p. 136°–138° C.) was prepared in a similar manner to that demonstrated in the preparation of 5,6-dihydro-4-hydroxy-6-methyl 3-[(phenylmethyl)thio]-2H-naptho[1,2-b]pyran-2-one (Example 5) using the following: 6-(phenylmethoxy)indanone (1.50 g, 6.30 mmol), triethylamine (1.31 mL, 9.45 mmol), trimethylsilyltriflate (1.34 mL, 6.93 mmol), dichloromethane (20.0 mL) diethyl 2-(thiobenzyl)propane-1,3-dioate (0.825 g, 3.15 mmol). $^1$H NMR (400 MHz, DMSO-$d_6$) δ 7.526 (d, 1H, J=8 Hz), 7.483-7.461 (m, 2H), 7.403 (t, 2H, J=7 Hz), 7.350-7.314 (m, 1H), 7.278-7.177 (m, 6H), 7.110 (dd, 1 H, J=2 Hz, 8 Hz), 5.212 (s, 2H), 3982 (s, 2H), 3.588 (s, 2H).

EXAMPLE 12

9-Chloro-5,6-dihydro-4-hydroxy-3-[(phenylmethyl)thio]-2H-naptho[1,2-b]pyran-2-one The title compound (0.556 g, m.p. 169°–171° C.) was prepared in a similar manner to that demonstrated in the preparation of 5,6-dihydro-4-hydroxy-6-methyl-3[(phenylmethyl)thio]-2H-naphthol[1,2-b] pyran-2-one (Example 5) using the following: 7-hydroxy-1-tetralone (2.0 g, 11.0 mmol, W. M. Owton, *Synth. Commun.*, 21:981 (1991)), triethylamine (2.40 mL, 16.6 mmol), trimethylsilyltriflate (2.35 mL, 12.2 mmol), dichloromethane (25 mL) diethyl 2-(thiobenzyl) propane-1,3-dioate (1.45 g, 5.50 mmol). $^1$H NMR (400 MHZ, DMSO-$d_6$) δ 7.578 (d, 1H, J=2 Hz) 7.454 (dd, 1H, J=2 Hz, 8 Hz), 7.350 (d, 1H, J=8 Hz), 7.298-7.187 (m, 5H), 3.988 (s, 2H), 2.853 (t, 2H, 8 Hz), 2.602 (t, 2H, J=8 Hz).

EXAMPLE 13

6,7-Dihydro-4-hydroxy-3-[(phenylmethyl)thio]benzo[6,7]cyclohepta[1,2-b]pyran-2 (5H)-one The title compound (0.491 g, m.p. 108°–110° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 1-benzosuberone (2.14 g, 13.37 mmol), triethylamine (2.80 mL, 20.0 mmol), trimethylsilyltriflate (2.85 mL, 14.7 mmol), dichloromethane (20 mL) diethyl 2-(thiobenzyl) propane-1,3-dioate (1.17 g, 4.46 mmol). $^1$H NMR (400 MHz, DMSO-$d_6$) δ 11.050 (bs, 1H), 7.561 (dd, 1H, J=1 Hz, 7 Hz), 7.449-7.368 (m, 3H), 7.272 7.195 (m, 5H), 3.976 (s, 2H), 2.554-2.500 (m, 2H), 2.161-2.052 (m, 4H).

EXAMPLE 14

4-Hydroxy-3-[(phenylmethyl)thio]-2H,5H-pyrano[3,2-c][1]bensopyran-2-one

The title compound (0.250 g, m.p. 166°–168° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 4-chromanone (3.00 g, 20.2 mmol), triethylamine (4.20 mL, 30.4 mmol), trimethylsilyltriflate (4.30 mL, 22.3 mmol), dichloromethane (30 mL) diethyl 2-(thiobenzyl) propane-1,3-dioate (1.57 g, 6.00 mmol). $^1$H NMR (400 MHz, DMSO-$d_6$) δ 7.566 (dd, 1H, J=1 Hz, 8 Hz), 7.413 (t, 1 H, J=7.5 Hz), 7.277-7.203 (m, 5H), 7.111 (td, 1 H, J=1H, 7.5 Hz), 6.966 (d, 1H, J=8 Hz), 5.066 (s, 2H), 3.959 (s, 2H).

EXAMPLE 15

5,6-Dihydro-4-hydroxy-8-(phenylmethoxy)-3-[(phenylmethyl)thio]-2H-naphtho[1,2-b]pyran-2-one The title compound (0.174 g, m.p. 123°–126° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 6-(phenylmethoxy)-1-tetralone (1.10 g, 4.37 mmol), triethylamine (0.91 mL, 6.5 mmol), trimethylsilyltriflate (0.93 mL, 22.3 mmol), dichloromethane (20 mL) diethyl 2-(thiobenzyl)propane-1,3-dioate (0.86 g, 3.3 mmol). $^1$H NMR (400 MHz, DMSO-$d_6$) δ 7.608 (d, 1H, J=8 Hz), 7.476-7.357 (m, 5H), 7.270-7.185 (m, 5H), 7.026-6.998 (m, 2H), 5.160 (s, 2H), 3.939(s, 2H), 2,824 (t, 2H, J=8 Hz), 2.553 (t, 2H, J=8 Hz).

EXAMPLE 16

4-Hydroxy-3-[(2-phenylethyl)thio]indeno[1,2-b]pyran-2(5H)-one

A suspension of 4-hydroxyindeno[1,2-b]pyran-2(5H)-one (0.250 g, 1.25 mmol) in ethanol (5.0 mL) was treated with triethylamine (0.40 mL, 3.0 mmol) and phenethyl-p-toluenethiosulfonate (0.470 g, 1.63 mmol, J. E. Dunbar, et al., U.S. Pat. No. 3,810,922). The resulting solution was then heated to reflux for 48 hours, allowed to cool, and the solvent removed in vacuo. The residue was then diluted with $H_2O$ (5.0 mL) and the product extracted with ethyl acetate (3×20 mL). The organic layers were combined, dried with $Na_2SO_4$, and the solvent removed in vacuo. The residue was then submitted to column chromatography ($SiO_2$-230 to 400 mesh, 1% MeOH in $CH_2Cl_2$) to provide the title compound (0.155 g, m.p. 160°–162° C.). $^1$H NMR (400 MHz, $CDCl_3$) δ 7.763-7.715 (m, 2H), 7.590-7.569 (m, 1H), 7.484-7.448 (m, 2H), 7.290-7.253 (m, 2H), 7.189-7.156 (m, 3H), 3.701 (s, 2H), 3.110 (t, 2H, J=7.5 Hz), 2.902 (t, 2H, J=7.5 Hz).

EXAMPLE 17

4-Hydroxy-3-[(2-phenoxyethyl)thio]-indeno[1,2-b]pyran-2(5H)-one

The title compound (0.047 g, m.p. 141°–142° C.) was prepared in a similar manner to that demonstrated in the preparation of 4-hydroxy-3-[(2-phenylethyl)thio]indeno[1, 2-b]pyran-2(5H)-one (Example 16) using the following: 4-hydroxyindeno[1,2-b]pyran-2 (5H)-one (0. 200 g, 1.00 mmol), 2-phenoxyethyl-1-p-toluenethiosulfonate (0.470 g, 1.50 mmol, J. E. Dunbar et al., U.S. Pat. No. 3,810,922), triethylamine (0.28 mL, 2.0 mmol), ethanol (5.0 mL). 'H NMR (400 MHz, DMSO-$d_6$) δ 7.683-7.657 (m, 2H), 7.495-7.473 (m, 2H), 7.231 (td, 2H, J=2 Hz, 7.5 Hz), 6.910-6.831 (m, 3H), 4.127 (t, 2H, J=6.5 Hz), 3.725 (s, 2H), 3.090 (t, 2H, J=6.5 Hz).

EXAMPLE 8

4-Hydroxy-3-[(2-phenylethyl)thio]-5-methylpyrano[3,2-b]indol-2(5H)-one

The title compound (0.069 g, m.p. 155°–157° C.) was prepared in a similar manner to that demonstrated in the preparation of 4-hydroxy-3-[(2phenylethyl)thio]-indeno[1,2-b]pyran-2(5H)-one (Example 16) using the following: 4-hydroxy-5-methylpyrano[3,2-b]indol-2(5H)-one (0.252 g, 1.17 mmol), (2-phenylethan-1-yl)-p-toluenethiosulfonate (0. 510 g, 1.76 mmol, J. E. Dunbar et al., U.S. Pat. No. 3,810,922 ) , sodium methoxide (0.095 g, 1.76 mmol), ethanol (15.0 mL). 'H NMR (400 MHz, DMSO-$d_6$) δ 7.773 (d, 1H, J=8 Hz), 7.650 (d, 1H, J=8.5 Hz), 7.449 (td, 1H, J=1 Hz, 7 Hz), 7.251-7.203 (m, 5H), 7.193-7.111 (m, 1H), 4.018 (s, 3H), 2.975 (t, 2H, J=7.5 Hz), 2.827 (t, 2H, 7.5 Hz).

EXAMPLE 19

5, 6-Dihydro-4,7-dihydroxy-3-[(phenylmethyl)thio]-2H-naphtho[1,2-b]pyran-2-one The title compound (0.223 g, m.p. 187°–190° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 5-hydroxy-1-tetralone (1.00 g, 6.17 mmol [J. D. Genzer, G. A. Conrad, U.S. 71-146852]), triethylamine (2.50 mL, 18.0 mmol), trimethylsilyltriflate (2.50 mL, 13.0 mmol), dichloromethane (50.0 mL) diethyl 2-(thiobenzyl)propane-1,3-dioate (0.808 g, 3.09 mmol). 'H NMR (400 MHz, DMSO-$d_6$) δ 11.190 (bs, 1H), 9.752 (s, 1H), 7.295-7.107 (m, 7H), 6.948-6.905 (m, 1H), 3.970 (s, 2H), 2.757 (t, 2H, J=8 Hz), 2.555 (t, 2 H, J=8 Hz).

EXAMPLE 20

[[5,6-Dihydro-4-hydroxy-2-oxo-3-[(phenylmethy)thio]-2H-naphtho[1,2-b]pyran-8-yl]oxy]-acetic acid A solution of ethyl-[(5,6,7,8-tetrahydro-5-oxo-2-naphthalenyl)oxy]-acetate (1.75 g, 7.05 mmol) in $CH_2Cl_2$ (40.0 mL) was cooled to 0° C. ($N_2$ atmosphere) and treated with triethylamine (3.00 mL, 21.0 mmol) followed by trimethylsilyltriflate (3.00 mL, 15.5 mmol). The solution was then warmed to ambient temperature, allowed to stir for 15 min., and subsequently quenched into a mixture of diethyl ether (50 mL) and saturated aqueous $NaHCO_3$ (20 mL). The layers were separated and the organic layer washed with a 1:1 mixture of brine: saturated $NaHCO_3$ (20 mL). The ethereal solution was then dried with $Na_2SO_4$ and the solvent removed in vacuo. The resulting silyl enol ether was then transferred to a flask containing diethyl 2-(thiobenzyl)propane-1,3-dioate (1.97 g, 7.52 mmol). The mixture was then heated to 160° C. for 16 h. and allowed to cool to room temperature where it was submitted to chromatography ($SiO_2$-230 to 400 mesh, 100% $CH_2Cl_2$ to 0.5% MeOH / $CH_2Cl_2$) to provide an impure solid which was diluted with diethyl ether (20 mL) and extracted with saturated $Na_2CO_3$ (3×20 mL). The combined aqueous extracts were washed with diethyl ether (3×50 mL) and then acidifed with conc. HCl to pH 0. The mixture was then extracted with dichloromethane (3×100 mL), the organic layers combined, dried with $Na_2SO_4$ and the solvent removed in vacuo to provide the title compound (0.125 g, m.p. 168°–171° C.). 'H NMR (400 MHZ, DMSO-$d_6$) δ 7.600 (d, 1 H, J=8 Hz) , 7.271-7.152 (m, 5H), 6.897 (s, 1H), 4.764 (s, 2H), 3.779 (s, 2H), 2.826 (t, 2H, J=8 Hz), 2.558 (t, 2H, J=8 Hz).

EXAMPLE 21

4-Hydroxy-3-[(3-phenylpropyl)thio]-2H-naphtho[1,2-b] pyran-2 -one

The title compound (0.093 g, m.p. 136°–138° C.) was prepared in a similar manner to that demonstrated in the preparation of 4-hydroxy-3-[(2-phenylethyl)thio]indeno[1,2-b]pyran-2-(5H) -one (Example 16) using the following: 4-hydroxy-2H-naphtho[1,2-b]pyran-2-one (0.200 g, 0.934 mmol), (3-phenylprop-1-yl)-p-toluenethiosulfonate (0.490 g, 1.59 mmol, J. E. Dunbar et al., U.S. Pat. No. 3,810,922), triethylamine (0.11 mL, 1.12 mmol), sodium bicarbonate (0.090 g, 1.20 mmol), ethanol (20.0 mL). 'H NMR (400 MHz, $CDCl_3$) δ 7.892-7.859 (m, 2H), 7.375-7.159 (m, 7H), 2.964-2.924 (t, 2H, J=8 Hz), 2.825-2.704 (m, 6H), 1.943-1.868 (quint, 2H, J=7.5 Hz) .

EXAMPLE 22

4-Hydroxy-3-[(phenylmethyl)thio]-6-methylindeno[1,2-b]pyran-2(5H)-one

The title compound (0.311 g, m.p. 167°–169° C.) was prepared in a similar manner to that demonstrated in the preparation of 5,6-dihydro-4-hydroxy-6-methyl3-[(phenylmethyl)thio]-2H-naphtho[1,2-b]pyran-2-one (Example 5) using the following: 4-methyl-1-indanone (1.00 g, 6.17 mmol), triethylamine (1.17 mL, 5.62 mmol), trimethylsilyltriflate (1.30 mL, 6.74 mmol) , dichloromethane (30.0 mL) diethyl 2-(thiobenzyl)propane-1,3-dioate (0.736 g, 2.81 mmol). 'H NMR (400 MHz, DMSO-$d_6$) δ 7.477 (d, 1H, J=7.5 Hz), 7.390 (t, 1H, J=7.5 Hz), 7.306-7.183 (m, 6 H), 3,977 (s, 2H), 3.547 (s, 2H), 2.360 (s, 3H).

EXAMPLE 23

6-Bromo-4 -hydroxy-3-[(phenylmethyl)thio]indeno[1,2-b]pyran-2(5H)-one

The title compound (0.069 g, m.p. 177°–179° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 4-bromo-1-indanone (2.0 g, 9.48 mmol (M. Adamczyk, D. S. Watt, D. A. Netzel, J. Org. Chem., 49:4226 (1984)), triethylamine (2.60 mL, 18.96 mmol), trimethylsilyltriflate (2.74 mL, 14.22 mmol), dichloromethane (40.0 mL) diethyl 2-(thiobenzyl)propane-1,3-dioate (0.830 g, 3.16 mmol). 'H NMR (400 MHz, DMSO-$d_6$) δ 7.698-7.665 (m, 2H), 7.438 (t, 1H, J=8 Hz), 7.295-7.164 (m, 5H), 4.005 (s, 2H), 3.632 (s, 2H).

EXAMPLE 24

5,6-Dihydro-4,9-dihydroxy-3-[(phenylmethyl)thio]-2H-naphtho[1,2-b]pyran-2-one The title compound (0.409 g, m.p. 226°–228° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 7-hydroxy-1-tetralone (1.5 g, 9.25 mmol (M. Mosettig, *J. Org. Chem.*, 5: 528, 533 (1940)), triethylamine (5.20 mL, 37.0 mmol), trimethylsilyltriflate (4.10 mL, 21.3 mmol), dichloromethane (40.0 mL) diethyl 2- (thiobenzyl)propane-1,3-dioate (1.21 g, 4.63 mmol). 'H NMR (400 MHZ, DMSO-$d_6$) δ 9.592 (bs, 1H), 7.282-7.197 (m, 5H), 7.121-7.087 (m, 2H), 6.685 (dd, 1H, J=2.6 Hz, J=8 Hz), 3.972 (s, 2H), 2.729 (t, 2H, 7.5 Hz), 2,553 (t, 2H, J=7.5 Hz).

EXAMPLE 25

4-Hydroxy-3-[(phenylmethyl)thio]-2H,5H-[1]bensothiopyrano[4,3-b]pyran-2-one

The title compound (0.453 g, m.p. 142°–144° C.) was prepared in a similar manner to that demonstrated in the preparation of 5,6-dihydro-4-hydroxy-6-methyl-3-[(phenylmethyl)thio]-2H-naphtho[1,2-b] pyran-2-one (Example 5) using the following: thiochroman-4-one (3.0 g, 18.27 mmol), triethylamine (5.10 mL, 36.5 mmol), trimethylsilyltriflate (3.90 mL, 20.1 mmol), dichloromethane (35.0 mL) diethyl 2-(thiobenzyl)propane-1,3-dioate (1.60 g, 6.09 mmol.) . 'H NMR (400 MHz, DMSO-$d_6$) δ 7.755 (d, 1H, J=7.5 Hz), 7.404-7.388 (m, 2H), 7.372-7.217 (m, 5H), 3.985 (s, 2H), 3.838 (s, 2H).

EXAMPLE 26

4-Hydroxy-3-[(phenylmethyl)thio]-2H,6H-[2]bensothiopyrano[4,3-b]pyran-2-one

The title compound (0.142 g, m.p. 68°–70° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 2-isothiochroman-4-one (2.000 g, 12.18 mmol), triethylamine (3.40 mL, 24.4 mmol), trimethylsilyltriflate (3.00 mL, 15.8 mmol), dichloromethane (35.0 mL), diethyl 2-(thiobenzyl)propane-1,3-dioate (1.06 g, 4.06 mmol.). 'H NMR (400 MHz, DMSO-$d_6$) δ 7.700 (dd, 1H, J=1.5 Hz, 8 Hz), 7.695-7.440 (m, 2H), 7.376 (dd, 1H, J=1 H, J=8 Hz).

EXAMPLE 27

9-Chloro-5,6-dihydro-4,7-dihydroxy-3-[(phenylmethyl)thio]-2H-naphtho[1,2-b]pyran-2-one The title compound (0.089 g, m.p. 247°–249° C. (dec.) ) was prepared in a similar manner to that demonstrated in the preparation of 5,6-dihydro-4-hydroxy-6-methyl-3-[(phenylmethyl)thio]-2H-naphtho[ 1,2-b]pyran-2-one(Example 5) using the following: 7-chloro-3,4-dihydro-5-hydroxy-1(2H)-naphthalenone (1.50 g, 7.63 mmol, Schender et al., *J. Med. Chem.*, 16:254 (1973)), triethylamine (3.20 mL, 22.9 mmol), trimethylsilyltriflate (3.00 mL, 15.8 mmol), dichloromethane (35.0 mL), diethyl 2-(thiobenzyl)propane-1,3-dioate (1.30 g, 5.04 mmol.). 'H NMR (400 MHz, DMSO-$d_6$) δ 11.380 (bs, 1H), 10.074 (bs, 1H), 7.297-7.196 (m, 5H), 7.096 (d, 1H, J=2.5 Hz), 6.906 (d, 1H, J=2.5 Hz), 3.981 (s, 2H), 2.823 (t, 2H, J=8 Hz), 2.598 (t, 2H, J=8 Hz).

EXAMPLE 28

7-Fluoro-4-hydroxy-3-[(phenylmethyl)thio]indeno[1,2-b]pyran-2(5H)-one

The title compound (0.060 g, m.p. 170°–173° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 5-fluoro-1-indanone (1.29 g, 8.59 mmol), triethylamine (2.40 mL, 17.2 mmol), trimethylsilyltriflate (2.50 mL, 12.9 mmol), dichloromethane (30.0 mL) , diethyl 2-(thiobenzyl)propane-1,3-dioate (1.13 g, 4.30 mmol.). 'H NMR (400 MHz, DMSO-$d_6$) δ 7.682 (dd, 1H, J=5 Hz, J =8.7 Hz), 7.535 (dd, 1H, J=2 Hz, J=8.8 Hz), 7.339-7.160 (m, 6H), 3.981 (s, 2H), 3.695 (s, 2 H).

EXAMPLE 29

[[2,5-Dihydro-4-hydroxy-2-oxo-3-[(phenylmethyl)thio]indeno[1,2-b]pyran-8]oxy]-acetic acid The title compound (0.157 g, m.p. 75°–77° C.) was prepared in a similar manner to that demonstrated in the preparation of [(5,6-dihydro-4-hydroxy-2-oxo-3-phenylmethy)thio]-2H-naphtho[1,2-b]pyran-8-yl]oxy]-acetic acid (Example 20) using the following: methyl[(2,3-dihydro-3-oxo-1H-inden-6-yl)oxy]acetate (1.00 g, 4.50 mmol), triethylamine (1.26 mL, 9.10 mmol), trimethylsilyltriflate (1.04 mL, 5.40 mmol), dichloromethane (20.0 mL), diethyl 2-(thiobenzyl)propane-1,3-dioate (0.59 g, 2.25 mmol.). 'H NMR (400 MHz, DMSO-$d_6$) δ 7.544 (d, 1H, J=8 Hz), 7.334-7.197 (m, 6H), 7.080-7.040 (m, 1H), 4.905 (s, 2H), 3.980 (s, 2H), 3.594 (s, 2H).

EXAMPLE 30

4-Hydroxy-3-[(phenylmethyl)thio]-6,8-dimethylindeno[1,2-b]pyran-2(5H)-one

The title compound (0.087 g, m.p. 179°–181° C.) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 4,6-dimethylindanone (0.55 g, 3.43 mmol, Wagner-Jauregg, Arnold, Hueter, *Chem Ber.*, 75: 1293, 1295 (1942)), triethylamine (0.96 mL, 6.88 mmol), trimethylsilyltriflate (0.80 mL, 4.12 mmol), dichloromethane (10.0 mL), diethyl 2-(thiobenzyl)propane-1,3-dioate (0.45 g, 1.72 mmol.). 'H NMR (400 MHz, DMSO-$d_6$) δ 7.298 (s, 1H), 7.282-7.175 (m, 5H), 7.110 (s, 1H), 3.978 (s, 2H), 3.517 (s, 2H), 2.367 (s, 3H), 2.317 (s, 3H).

EXAMPLE 31

[[2,5-Dihydro-4-hydroxy-2-oxo-3-[(phenylmethyl)thio]indeno[1,2-b]pyran-6-yl]oxy]-acetic acid The title compound (0.497 g, m.p. 233°–236° C.) was prepared in a similar manner to that demonstrated in the preparation of [[5,6-dihydro-4-hydroxy-2-oxo-3- phenylmethyl)thio]-2H-naphtho[1,2-b]pyran-8-yl]oxy]acetic acid (Example 20) using the following: methyl-[(2,3-dihydro-1-oxo-1H-inden-4-yl)oxy]acetate (1.50 g, 6.82 mmol), triethylamine (1.90 mL, 13.6 mmol), trimethylsilyltriflate (1.58 mL, 8.18 mmol), dichloromethane (20.0 mL), diethyl 2-(thiobenzyl)propane-1,3-dioate (0.89 g, 3.41 mmol.). ¹H NMR (400 MHz, DMSO-d⁶) δ 7.429 (t, 1H, J=7.5 Hz), 7.300-7.149 (m, 6H), 7.035 (d, 1H, J=8 Hz), 4.841 (s, 2H), 3.989 (s, 2H), 3.597 (s, 2H).

EXAMPLE 32

3-[(Cyclopropylmethyl)thio]-4-hydroxyindeno[1,2-b]pyran-2(5H)-one

The title compound (0.047 g, m.p. 145°–146° C.) was prepared in a similar manner to that demonstrated in the preparation of 4-hydroxy-3-[(2-phenylethyl)thio]-indeno[1,2-b]pyran-2(5H)-one (Example 16) using the following: 4-hydroxy-indeno[1,2-b]pyran-2(5H)-one (0.250 g, 1.24 mmol), (cyclopropylmethyl)-p-toluenethiosulfonate (0.720 g, 2.11 mmol), triethylamine (0.13 mL, 2.11 mmol), sodium bicarbonate (0.103 g, 1.24 mmol), ethanol (10.0 mL). ¹H NMR (400 MHz, CDCl₃) δ 8.080 (bs, 1H), 7.762-7.729 (m, 1H), 7.593-7.562 (m,1H), 7.485-7.423 (m, 2H), 3.732 (s, 2H), 2.700 (d, 2H, J=11.2 Hz), 1.019-0.942 (m, 1H), 0.582-0.536 (m, 2H), 0.256-0.217 (m, 2H).

EXAMPLE 33

4-Hydroxy-3-[(3-phenylpropl)thio]indeno[1,2-b]pyran-2(5H)-one

The title compound (0.012 g, m.p. 152°–153° C.) was prepared in a similar manner to that demonstrated in the preparation of 4-hydroxy-3-[(2-phenylethyl) thio]indeno[1,2-b]pyran-2(5H)-one (Example 16) using the following: 4-hydroxy-indeno[1,2-b]pyran-2(5H)-one (0.300 g, 1.49 mmol), (3-phenyl-n-propan-1-yl)-p-toluenethiosulfonate (0.780 g, 2.54 mmol, J. E. Dunbar et al., U.S. Pat. No. 3,810,922), triethylamine (0.15 mL, 1.49 mmol), ethanol (10.0 mL). ¹H NMR (300 MHz, CDCl₃) δ 7.990 (bs, 1H), 7.766-7.7736 (m, 1H), 7.598-7.569 (m, 1H), 7.469-7.444 (m, 2H), 7.304-7.207 (m, 2H), 7.1865-7.159 (m, 3H), 3.722 (s, 2H), 2.811 (t, 2H, J=8 Hz), 2.731 (t, 2H, J=8 Hz), 1.937 (quint., 2H, J=8 Hz).

EXAMPLE 34

4-Hydroxy-3-[(2-phenylethyl)thio]-2H-naphtho[1,2-b]pyran-2-one

The title compound (0.004 g, m.p. 113°–114° C.) was prepared in a similar manner to that demonstrated in the preparation of 4-hydroxy-3-[(2-phenylethyl)thio]-indeno[1,2-b]pyran-2(5H)-one (Example 16) using the following: 4-hydroxy-2H-naphtho[1,2-b]pyran-2-one (0.300 g, 1.49 mmol), (2-phenylethan-1-yl)-p-toluenethiosulfonate (0.620 g, 2.68 mmol, J. E. Dunbar et al., U.S. Pat. No. 3,810,922), triethylamine (0.15 mL, 1.49 mmol), sodium bicarbonate (0.128 g, 1.54 mmol), ethanol (20.0 mL). ¹H NMR (300 MHz, CDCl₃) δ 7.904 (d, 1H, J=8.5 Hz), 7.880 (d, 1H, J=2 Hz), 7.695-7.181 (m, 7H), 3.148-3.098 (m, 2H), 2.977-2.889 (m, 4H), 2.792-2.738 (m, 2H).

EXAMPLE 35

4-Hydroxy-3-[phenylthio]indeno[1,2-b]pyran-2(5H)-one

The title compound (0.475 g, m.p. 228°–230° C. (dec.)) was prepared in a similar manner to that demonstrated in the preparation of 5,6-dihydro-4-hydroxy-6-methyl-3-[(phenylmethyl)thio]-2H-naphtho[1,2-b]pyran-2-one (Example 5) using the following: 1-indanone (2.0 g, 15.13 mmol), triethylamine (4.22 mL, 30.3 mmol), trimethylsilyltriflate (3.50 mL, 18.2 mmol), dichloromethane (40.0 mL), diethyl 2-(thiophenyl)propane-1,3-dioate (1.34 g, 5.0 mmol, T. Fujisawa, Chem. Lett., 287 (1973)). ¹H NMR (400 MHz, DMSO-d₆) δ 7.723-7.687 (m, 2H), 7.546-7.478 (m, 2 H), 7.290-7.252 (m, 2H), 7.174-7.111 (m, 3H), 3.799 (s, 2H).

EXAMPLE 36

4-Hydroxy-3-[phenylthio]-2H-naphtho[1,2-b]pyran-2-one

A solution of thiophenol (0.19 mL, 1.60 mmol) in CH₂Cl₂ (10.0 mL) at 0° C. (N₂ atmosphere) was treated with N-chlorosuccinimide (0.200 g, 1.49 mmol). The mixture was allowed to stir for 15 min then treated with 4-hydroxy-2H-naphtho[1,2-b]pyran-2-one (0.200 g, 0.934 mmol) and triethylamine (0.802 g, 2.33 mmol). The resulting mixture was then allowed to warm to ambient temperature where it was stirred for 2 h. The solution was then poured into saturated sodium carbonate (30.0 mL) and washed with diethyl ether (3×50 mL). The aqueous layer was then acidified with 4N HCl to pH 1 then extracted with CH₂Cl₂ (2×50 mL). The organic layers were combined, dried with Na₂SO₄ and the solvent removed in vacuo. The resulting residue was then submitted to column chromatography (SiO₂-230 to 400 mesh, 100% CH₂Cl₂ to 1% MeOH to provide the title compound (0.023 g, m.p. 182°–183° C.). ¹H NMR (300 MHz, CDCl₃) δ 7.924 (d, 1H, J=7.2 Hz), 7.385-7.209 (m, 8H), 2.980 (t, 2H, J=8.3 Hz), 2.823 (t, 2H, J=8.3 Hz).

The biological activity of the subject compounds was determined in an HIV Protease Inhibition Assay.

Determination of HIV Protease Inhibition

Starting Materials

DTT Buffer: 1.0 mM dithiothreitol (DTT) was prepared fresh daily in 0.1% polyethylene glycol (mw 8000) 80 mM NaOAc, 160 mM NaCl, 1.0 mM EDTA, and brought to pH 4.7 with HCl.

HIV-1 Protease: The enzyme is obtained from Bachem Bioscience Inc. The undiluted enzyme is thawed from −80° C. and diluted 50-fold with DTT buffer. The solution is always kept at 0° C. on ice water and used in the experiment within 20 minutes after thawing.

Ensyme Substrates: Substrate III from Bachem Bioscience Inc. is the undecapeptide H-His-Lys-Ala-Arg-Val-Leu-p-Nitrophenylalanine-Glu-Ala-Norleucine-Ser-NH2 (>97% purity). A 200 μM stock solution in DTT buffer is prepared and stored on ice. Substrate solution is prepared fresh daily.

Test Compound: 10 mM inhibitor (I) in dimethyl sulfoxide (DMSO) is diluted to 200 μM with DTT buffer. From the 200 μM stock solution is made a 10 μM stock solution with 2% DMSO in DTT buffer. The two inhibitor solutions are used to make final [I]=100, 50, 20, 10, 5, 2, 1, 0.5 and 0 μM with 2% DMSO in DTT buffer in each reaction well (total inhibitor volume of 50 μl).

Assay

To each reaction well is added 20 μl of substrate (final concentration of 40 μM), 50 μl of inhibitor (at a concentration such that final dilution will produce the test concentration) and 20 μl of DTT buffer. The reaction plate (96 wells) is incubated at 37° C. for at least 5 minutes.

10 μl of the diluted protease is added to the reaction well while the reaction plate is shaking. Once shaken for 10 seconds, the plate is returned to the heating block at 37° C. (final reaction volume 100 μl.)

The reaction is incubated for 5 minutes at 37° C. The reaction is stopped by placing the reaction plate on the shaker and adding 20 μl of 10% trifluoroacetic acid (TFA) and shaking for 10 seconds. The amount of proteolysis is then determined by separation of noncleaved substrate and two cleaved products with reverse-phase HPLC, while measuring absorbance at 220 nm to determine the relative peak areas of the three components. The relative peak areas are used to calculate % conversion to product as a function of inhibitor concentration. The data is plotted as % Control (the ratio of % conversion is the presence and absence of inhibitor×100) versus inhibitor concentration and fit with the equation $Y=100/1+(X/IC_{50})^A$, where $IC_{50}$ is the inhibitor concentration at 50% inhibition and A is the slope of the inhibition curve.

The results are listed in Table I.

TABLE I

HIV PROTEASE INHIBITION RESULTS

| EXAMPLE | 50% INHIBITION CONCENTRATION [μM] |
|---|---|
| 1 | 1.3 |
| 3 | 0.7 |
| 4 | 1.4 |
| 6 | 2.0 |
| 9 | 2.5 |
| 11 | 2.2 |
| 14 | 4.0 |
| 16 | 3.5 |
| 25 | 1.3 |
| 29 | 1.4 |

It should be apparent to those skilled in the art that other compositions not specifically disclosed in the instant specification are, nevertheless, contemplated thereby. Such other compositions are considered to be within the scope and spirit of the present invention. Hence, the invention should not be limited by the description of the specific embodiments disclosed herein but only by the following claims.

What is claimed is:

1. A compound, or a pharmaceutically acceptable salt thereof, of Formula

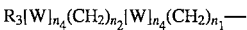

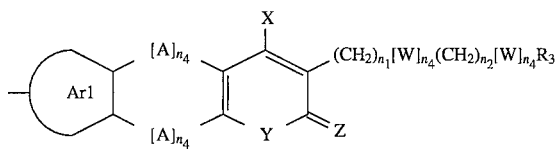

wherein $X$ is $OR_1$, $NHR_1$, $SH$, $CH_2OR_1$, or $CO_2H$ wherein $R_1$ is hydrogen or $COR_2$ wherein $R_2$ is a straight chain alkyl moiety 1 to 5 carbon atoms in length, a branched alkyl moiety containing three to five carbon atoms, a cyclic alkyl moiety containing three to six carbon atoms, phenyl, or a hydrogen atom;

$Y$ is oxygen;

$Z$ is oxygen or sulfur;

$W$ is oxygen, $NR_3$, $C(R_3)_2$, $NCO(V)_{n4}R_3$, $CO$, $HC=CH$, $S(O)_{n3}$, $C\equiv C$, $NR_3COV_{n4}$, or $CR_3OR_3$ wherein v is oxygen, sulfur, $NR_3$ or $CHR_3$ wherein $R_3$ is hydrogen, $(CH_2)_{n3}R_4$, or $(CH_2)_{n3}Ar$ wherein $R_4$ is hydrogen, a straight or branched alkyl moiety containing one to five carbon atoms, a cyclic alkyl moiety containing 3 to 6 carbon atoms, phenyl or the substituted derivatives thereof wherein the substituents are one or more of $CO_3R_2$, $CON(R_2)_2$, F, $OR_2$, phenyl, naphthyl, or $CF_3$;

Ar is a 5- or 6-membered ring containing zero heteroatoms, a fused ring of 8–10 atoms containing zero heteratoms or the substituted derivatives thereof wherein the substituents are of F, Cl, Br, $OR_4$, $N(R_4)_2$, $CO_2R_1$, $CON(R_1)_2$, $COR_4$, $R_4$, $OCH_2O$, $OCH_2CH_2O$, or $C\equiv N$;

A1 is a 5- or 6- membered ring containing zero heteratoms or a fused ring of 8–10 carbon atoms containing zero heteroatoms;

n1, n2, n3 and n4 are integers of from 0 to 4, 0 to 3, 0 to 2, and 0 to 1, respectively, with the provisos that n2 is zero when an intra-chain n4 is zero, and n2 is 2 to 4 when two intrachain groups W are heteroatoms;

A is $T_{n6}C(R_3)_2T_{n4}$ wherein $T=C(R_3)_2$ and the central ring of the tricycle is a 5-, 6-, 7-, or 8-membered ring.

2. A compound of the formula in claim 1 wherein

X is hydroxy;

Z is oxygen;

Y is oxygen;

W is oxygen, $NR_3$, $C(R_3)_2$, $S(O)_{n3}$, $CR_3OR_3$, or $CH=CH$ wherein $R_3$ is hydrogen, $(CH_2)_{n3}R_4$, or $(CH_2)_{n3}Ar$; $R_4$ is hydrogen, unsubstituted or substituted straight or branched alkyl containing 1 to 5 carbon atoms, cycloalkyl containing 3 to 6 carbon atoms, or phenyl wherein the substituents are of F, $CO_2H$, OMe, OH, $OCH_2CH_3$, or phenyl;

Ar1 is phenyl or cyclohexane;

Ar is unsubstituted or substituted phenyl, wherein the substituents are of F, Cl, Br, $OR_4$, $CO_2R_4$, $R_4$ or $OCH_2O$;

n1, n2, n3 and n4 are integers of from 0 to 4, 0 to 3, 0 to 2, and 0 to 1 respectively;

the central ring of the tricycle is a 5-, 6- or 7-membered ring; and

A is $(CH_2)_3$, $CH_2CHR_3$, $CHR_3CH_2$, or $CHR_3$.

3. A compound of the formula in claim 1 wherein

X is hydroxy;

Z is oxygen;

Y is oxygen;

W is oxygen, sulfur, $NR_3$, or $C(R_3)_2$ wherein $R_3$ is H, $(CH_2)_{n3}R_4$, or $(CH_2)_{n3}Ar$;

Ar1 is phenyl;

Ar is unsubstituted or substituted phenyl, wherein the substituents are one or more of F, Cl, $OR_4$, $CO_2R_4$, $R_4$, or $OCH_2O$, wherein $R_4$ is H, or unsubstituted or substituted $CH_3$, $CH_2CH_3$, $(CH_2)_3$, $(CH_3)_2CH$, $(CH_3)CHCH_2$, or $C_6H_5$ wherein the substituents are one or more of $CO_2H$, F, OMe, OH, or $CF_3$;

n1, n2, n3 and n4 are integers of from 0 to 2, 0 to 3, 0 to 2, and 0 or 1 respectively;

the central ring of the tricycle is a 5- or a 6-membered ring; and

A is $CH_2$, CHR, and $CHR_3CH_2$.

4. A compound selected from the group consisting of 5,6-Dihydro-4,8 -dihydroxy-3-[(phenyl-methyl)thio]-2H-naphtho[1,2-b]pyran-2-one, 5,6-Dihydro-4-hydroxy-7,9- dimethyl-3-[phenylmethyl)thio]-2H-naphtho[1,2-b]pyran-2-one, 4,8-Dihydroxy-3-[(phenylmethyl)thio]indeno[1,2-b]pyran-2(5H)-one, [[5,6-Dihydro-4-hydroxy-2-oxo-3-[(phenylmethyl)-2-H-naphtho[1,2-b]pyran-8-yl]oxy]acetic acid, 5,6-Dihydro-4,7-dihydroxy-3-[(phenylmethyl)thio]-2H-naphtho[1,2 -b]pyran-2-one, 4-Hydroxy-3-[(2 -pheny-1-[(phenylmethyl)thio]ethylindeno[1,2,-b]pyran-2-(5H)-one, 4-Hydroxy-3-[(3-methyl-1-phenylbutyl)thio]-indeno[1,2-b]pyran-2(5H)-one, 4,5-Dihydroxy-3-[3-methyl-1[(phenylmethyl)thio] butyl]indeno[1,2-b]pyran-2(5H-)one 5,6-Dihydro-4-hydroxy-5-(hydroxymethyl)-3-[2-phenyl-1-[(phenylmelthyl)thio]ethyl-2H-naphtho [1,2-b]pyran-2-one, and 4-Hydroxy-3-[(phenylmethyl)thio]-2H, 6H-[2]benzothiopyrano[4,3-b]pyran-2-one.

5. A pharmaceutical composition for the treatment of infection or disease caused by a retrovirus, which comprises an effective amount of the compound of claim 1 sufficient to provide an antivirally effective dosage of the compound in the range of about 1 to about 50 mg/kg-day and a pharmaceutically acceptable carrier.

6. A pharmaceutical composition for the treatment of infection or disease caused by a retrovirus, which comprises the compound of claim 1 sufficient to provide a steady state peak plasma concentration of the compound in the range of about 1–50 μM and a pharmaceutically acceptable carrier.

7. A method of treatment of infection or disease caused by a retrovirus, which comprises administering to a subject in need of such treatment an effective amount of a composition of claim 1.

8. A pharmaceutical composition for the treatment of infection or disease caused by a retrovirus, which comprises an effective amount of the compound of claim 1 which composition if tested in an in vitro protease inhibition assay is equivalent to 20 percent or greater of the concentration of the compound of claim 1 required to reduce the protease activity by fifty percent and a pharmaceutically acceptable carrier.

9. The pharmaceutical composition of claim 5 to be used in the treatment of an infection caused by HIV.

10. The pharamceutical composition of claim 5 to be used in the treatment of AIDS.

* * * * *

UNITED STATES PATENT AND TRADEMARK OFFICE
CERTIFICATE OF CORRECTION

PATENT NO. : 5,504,104
DATED : Apr. 2, 1996
INVENTOR(S) : Edmund L. Ellsworth, et al It is certified that error appears in the above-indentified patent and that said Letters Patent is hereby corrected as shown below:

Column 27, last line, the " v " after " wherein " should be a capital letter.

Column 28, line 7, the first subscript 3 should be subscript 2.

Column 28, line 12, the two subscript 1's should each be subscript 4.

Column 28, line 14, the first word should be " Ar1 " not " A1 ".

Column 28, line 21, the subscript n6 should be subscript n4.

Signed and Sealed this

Ninth Day of July, 1996

Attest:

BRUCE LEHMAN

Attesting Officer

Commissioner of Patents and Trademarks